United States Patent [19]

Gull et al.

[11] Patent Number: 5,538,971
[45] Date of Patent: Jul. 23, 1996

[54] BENZOQUINOXALINES, PHARMACEUTICAL COMPOSITIONS CONTAINING THEM AND THEIR USE IN TREATING SCHIZOPHRENIA

[75] Inventors: Peter Gull, Pfeffingen, Switzerland; Rudolf Markstein, Rheinfelden, Germany; Robert Swoboda, Köniz, Switzerland

[73] Assignee: Sandoz Ltd., Basel, Switzerland

[21] Appl. No.: 250,989

[22] Filed: May 27, 1994

Related U.S. Application Data

[63] Continuation-in-part of Ser. No. 983,013, Nov. 30, 1992, abandoned.

[30] Foreign Application Priority Data

Nov. 28, 1991 [DE] Germany .......................... 41 39 143.8

[51] Int. Cl.⁶ ...................... A61K 31/495; C07D 241/38
[52] U.S. Cl. ............................ 514/250; 544/344; 560/43; 564/428
[58] Field of Search ............................. 544/344; 514/250

[56] References Cited

FOREIGN PATENT DOCUMENTS 544240  6/1993  European Pat. Off. ............... 544/344

Primary Examiner—Mark L. Berch
Attorney, Agent, or Firm—Robert S. Honor; Melvyn M. Kassenoff; Joseph J. Borovian

[57] ABSTRACT

6-hydroxy or 6-alkoxy-1,2,3,4,4a,5,10,10a-octahydro-benzo[g]quinoxalines bearing in position 4 an optionally substituted phenyl group may be used in the treatment of schizophrenia, drug abuse or self-injurious behavior.

13 Claims, No Drawings

BENZOQUINOXALINES, PHARMACEUTICAL COMPOSITIONS CONTAINING THEM AND THEIR USE IN TREATING SCHIZOPHRENIA

This is a continuation-in-part of application Ser. No. 07/293,013, filed Nov. 30 1992, now abandoned.

The present invention relates to benzoquinoxalines, their production, their use as pharmaceuticals and pharmaceutical compositions containing them.

In particular the present invention provides 6-hydroxy or 6-alkoxy-1,2,3,4,4a,5,10,10a-octahydro-benzo[g]quinoxalines bearing in position 4 an optionally substituted phenyl group, in free base or acid addition salt form.

More particularly the present invention provides compounds of formula I

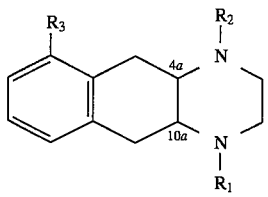

wherein $R_1$ is $(C_{1-4})$alkyl, $R_2$ is phenyl optionally mono-, di- or trisubstituted by halogen with an atomic number of 9 to 53, $(C_{1-4})$alkyl and/or $(C_{1-4})$alkoxy, and $R_3$ is hydroxy or $(C_{1-4})$alkoxy, in free base or acid addition salt form.

The compounds of formula I present two asymmetrical carbon atoms in positions 4a and 10a. They may therefore appear in racemic or optically active forms. The invention relates to all optical isomers and their mixtures including the racemic mixtures.

In positions 4a and 10a the compounds of formula I may have the cis configuration or the trans configuration. The compounds with the trans configuration are preferred. These include compounds with the configuration IA as well as compounds with the configuration IB

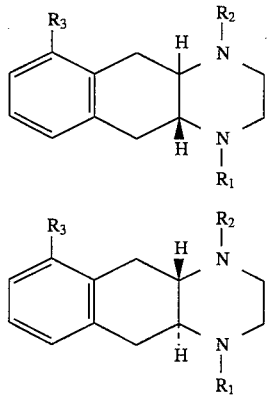

and the corresponding racemates.

The alkyl and alkoxy groups contained in the compounds of formula I preferably contain 1 or 2 carbon atoms, and in particular represent methyl or methoxy.

Halogen as defined above is preferably chlorine, bromine or fluorine.

$R_2$ preferably is a group of formula (a)

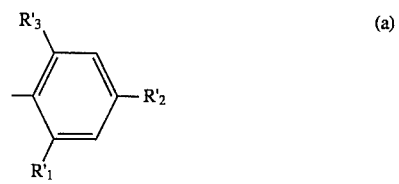

wherein $R'_1$ is hydrogen or $(C_{1-4})$alkyl, $R_2$ is hydrogen, halogen with an atomic number of 9 to 53 or $(C_{1-4})$alkyl, and $R_3$ is hydrogen or $(C_{1-4})$alkyl.

In a group of compounds of formula I, $R_1$ is $(C_{1-4})$alkyl, $R_2$ is a group of formula (a) and $R_3$ is hydroxy or $(C_{1-4})$alkoxy.

In accordance with the invention, the compounds of formula I and their salts are obtained, whereby a) in order to produce the compounds of formula Ia,

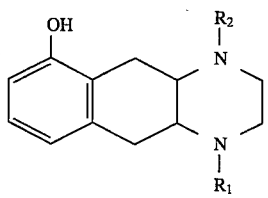

wherein $R_1$ and $R_2$ are defined as above, the ether group in compounds of formula Ib,

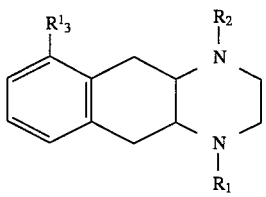

wherein $R_1$ and $R_2$ are defined as above, and $R^1_3$ is alkoxy with 1 to 4 carbon atoms, is cleaved, or b) in order to produce compounds of formula Ib, compounds of formula II,

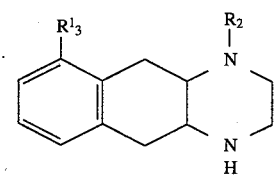

wherein $R_2$ and $R_3$ are defined as above, are alkylated, or c) in order to produce compounds of formula I'b

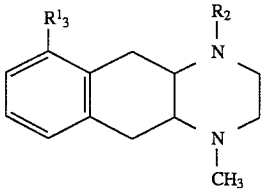

wherein $R_2$ and $R^1_3$ are defined as above, compounds of formula III,

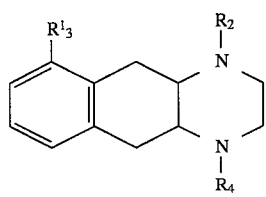

wherein $R_2$ and $R^1_3$ are defined as above, and $R_4$ is a radical which may be reduced to the methyl group, are reduced, and if desired, the compounds of formula I thus obtained are converted into their acid addition salts.

The ether cleavage according to process a) may be effected in known manner, for example using Lewis acids such as boron tribromide or strong mineral acids such as hydrobromic acid.

The alkylation according to process b) may similarly be effected in known manner, e.g. by a reaction with an alkyl halide. There may also be two stages, whereby first of all the compounds of formula II are acylated and then they are reduced.

The reduction according to process c) may be carried out by known methods. $R_4$ signifies for examples an alkoxycarbonyl or menthyloxycarbonyl group.

The enantiomer separation, if desired, may take place by known methods e.g. at the stage of the compounds of formula II or III. If $R_1$ is methyl, then introduction of the methyl group and splitting of the racemate may be carded out for example simultaneously, whereby in a compound of formula III, wherein $R_4$ signifies a menthyloxycarbonyl group, after separation of the diastereoisomers, the menthyloxycarbonyl radical is reduced to the methyl group, as described in example 1.

Working up of the reaction mixtures obtained and purification of the compounds of formula I thus produced may be carried out in accordance with known methods.

Acid addition salts may be produced from the free bases in known manner, and vice versa.

6-Hydroxy and 6-alkoxy-1,2,3,4,4a,5, 10, 10a-octahydrobenzo[g]quinoxalines not covered by formula I are obtained analogously to the preparation of the compounds of formula I.

The starting compounds of formulae II and III may be produced by known methods from compounds of formula IX [preparation analogous to Bull. Chem. Soc. Jap. 46, 985 (1973)] in accordance with the following reaction scheme, for example as described in example 1:

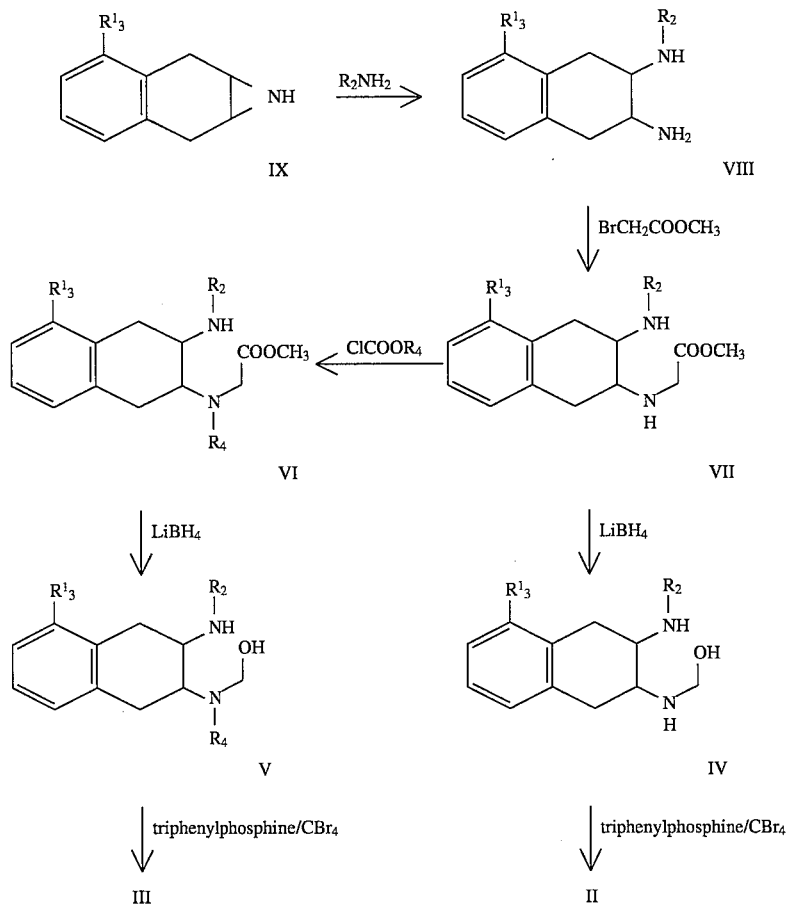

The starting compounds of formula IX are known or may be produced by known processes.

The 6-hydroxy or 6-alkoxy- 1,2,3,4,4a,5, 10, 10a-octahydrobenzo[g]quinoxalines bearing in position 4 an optionally substituted phenyl group and their physiologically acceptable acid addition salts, hereinafter referred to as compounds according to the invention, have interesting pharmacological properties when tested on animals, and may therefore be used as medicaments.

The compounds according to the invention exhibit antineuroleptic activity as indicated in standard tests, e.g. in inhibiting apomorphine induced rearing.

Thus when administered to the mouse at doses of ca. 0.05 to ca. 1 mg/kg p.o., there is observed a significant inhibition of the rearing induced by subcutaneous administration of 0.5 mg/kg of apomorphine. In this test, each mouse is contained in a glass cylinder (20 cm high, 8 cm diameter) on absorbent cardboard and rearing is quantified by accumulating the time spent with both forepaws off the ground during three 1-minute periods at 10 minute intervals after apomorphine administration. Test drugs are given 30 minutes before apomorphine. This test detects both classical and atypical anti-psychotics and thus has predictive value for efficacy in schizophrenia.

In the above mentioned apomorphine-induced rearing test, the compound of Example 2 had an $ED_{50}$ of 0.04 mg/kg s.c. and 0.14 mg/kg p.o. after 60 minutes. After 30 minutes the compound of Example 2 had an $ED_{50}$ of 0.033 mg/kg s.c. and 0.38 mg/kg p.o. Haloperidol after 30 minutes had an $ED_{50}$ of 0.008 mg/kg s.c. and 0.03 mg/kg p.o. and Clozapine an $ED_{50}$ of 0.66 s.c. and 4.3 p.o. After subchronic treatment for three consecutive days, the $E_{50}$ measured 60 minutes after the last administration was 0.28 mg/kg p.o. The compounds of the invention are therefore useful in the treatment of schizophrenia.

For this indication, the appropriate dosage will, of course, vary depending upon, for example, the compound employed, the host, the mode of administration and the nature and severity of the condition being treated. However, in general, satisfactory results in animals are indicated to be obtained at daily dosages from about 0.5 to about 50 mg/kg animal body weight. In larger mammals, for example humans, an indicated daily dosage is in the range from about 1 mg to about 300 mg of a compound according to the invention, conveniently administered, for example, in divided doses up to four times a day. An indicated daily dosage for the compound of Example 2 in the treatment of humans in schizophrenia, which is the preferred indication, is for example from 1 to 30 mg p.o.

The compounds according to the invention exhibit a selective dopamine antagonistic activity at receptors of the D-1 type (D-1 antagonistic activity), as evidenced by the following experimental data:

At concentrations of ca. 1 nmol/l to ca. 1 gmol/l the compounds according to the invention effect strong inhibition of the dopamine-induced stimulation of adenylate cyclase in homogenates of bovine retina [for the method see R. Markstein, Journal Neural. Transmission 51, 39–59 (1981)].

In the above mentioned functional test on adenylate cyclase, the compound of example 2 has a pKi of 7.3 (calculated from $IC_{50}$ according to Cheng and Prusoff, 1973). This activity also indicates the use of the compounds according to the invention in schizophrenia. Also the activity shows that the compounds are useful in drug abuse (especially cocaine abuse) or to antagonize the drug activity in case of a relapse, and also for the treatment of self-injurious behavior.

The D-1 selective antagonism is confirmed in the rat where at doses of ca. 0.1 to 10 mg/kg p.o. or ca. 0.1 to 0.5 mg/kg s.c. the compounds according to the invention inhibit the locomotor activity increase which was induced by administering 10 mg/kg p.o. of the D-1 agonist (−)-(6aR, 12bR)-4,6,6a,7,8,12b-hexahydro-7-methylindolo[4,3-ab] phenanthridine. In this test, the substance to be tested is applied one hour before the D-1 agonist, and the locomotor activity is measured under red light using photoelectric cells. Since clozapine is active in this test, it is considered to possess predictive value for antipsychotic drug activity.

In this test the compound of Example 2 inhibits the locomotor activity increase more potently than the known preferential D-1 antagonists Clozapine and (+)-(5R)[5β, 9α, 10α]-2-chloro-6-methyl-9-phenylergoline. With the compound of Example 2 the inhibition was 76% at 1 mg/kg p.o. whereas it was only 45% at 2 mg/kg p.o. with the phenylergoline, which in turn is more active than Clozapine (61% at 0.1 mg/kg i.p. versus 70% at 1 mg/kg i.p.).

Furthermore at doses of ca. 1 to ca. 10 mg/kg p.o., the compounds according to the invention effect no catalepsy of the rat. Cataleptogenic activity is assessed as described by G. Stille et al. in Arzneimittel Forschung 15, 841–843 (1965). The criterion for catalepsy is fulfilled when posture retention time is longer than 10 seconds. In view of the lack of cataleptogenic activity, the risk that the compounds according to the invention might cause extra-pyramidal side effects is improbable.

At 1, 3.2 and 10 mg/kg p.o., the compound of Example 2 fails to produce catalepsy during an observation period of 8 hours in the rat.

The compounds according to the invention may be administered by any conventional route, in particular enterally, preferably orally, for example in the form of tablets or capsules, or parenterally, for example in the form of injectable solutions or suspensions.

The present invention also provides pharmaceutical compositions comprising a compound according to the invention in association with at least one pharmaceutical carrier or diluent. Such compositions may be manufactured in conventional manner. Unit dosage forms contain, for example from about 0.25 mg to about 150 mg of a compound according to this invention.

The present invention furthermore provides a method of treating schizophrenia, drug abuse or self-injurious behavior in a subject in need of such treatment, which comprises administering a therapeutically effective amount of a compound according to the invention.

The compound of Example 2 is preferred.

The following examples illustrate the invention. The temperatures are given in degrees Celsius and are uncorrected.

EXAMPLE 1

(−)-[4aR,10aR 1-1,2,3,4,4a,5,10,10a-octahydro-4-(4'-chloro-2'-methyl-phenyl)-6-methoxy-1-methyl-benzo[g]quinoxaline a) trans-2-amino-3-(5'-chloro-2'-toluyl-amino)-5-methoxy-tetralin 1.1 ml (8.8 mM) of boron trifluoride ethyl etherate are added in drops at 0° to a solution of 1.5 g (8.5 mM) of 2,3-imino-5-methoxy-tetralin and 1.6 g (11.3 mM) of 4-chloro-2-methylaniline in 40 ml of 2-propanol. After stirring for 20 hours at room temperature, the solution is poured onto ice/water, neutralized with potassium bicarbonate solution, extracted with toluene/ethyl acetate 1:1 and washed with sodium chloride solution. The organic phases are dried over $Na_2SO_4$, filtered and concentrated by evaporation. 2.7 g of diamine are obtained, and are chromatographed on silica gel with ethyl acetate/ethanol 97:3, containing 0.01% conc. NH$_3$. The yield is 1.2 g of the desired regio-isomers (title compound).

NMR (CDCl$_3$, 360 MHz) δ2.13 (s, 3H), 2.37 (dd, J$_1$=18 Hz, J$_2$=8 Hz, 1H), 276 (dd, J$_1$= 18 Hz, J$_2$=11 Hz, 1H), 3.42 (dd, J$_1$=18 Hz, J$_2$=6 Hz, 1H), (s, 3H), 6.71 (m, 3H), 7.06 (m, 2H), 7.13 (t, J=7 Hz, 1H).

b) trans-2-methoxycarbonylmethylamino-3-(5'-chloro-2'-toluyl-amino)-5-methoxy-tetralin 522 mg (3.4 mM) of bromoacetic acid methyl ester in 20 ml of DMF are added at 0° to a suspension of 1.08 g (3.4 mM) of trans-2-amino-3-(5'-chloro- 2'-toluyl-amino)-5-methoxy-tetralin and 1.5 g of K$_2$CO$_3$, and subsequently stirred for 2 hours at room temperature. Working up is effected by filtering through Hyflo and evaporating the filtrate to dryness. The 1.77 g of raw product are chromatographed on silica gel with hexane/ethyl acetate 2:1. The yield is 0.52 g of the title compound, which is further used directly.

c) 76 ml (304 mM) of 4N NaOH are added in drops at 0° to a solution of 118 g (304 mM) of trans-2-methoxy-carbonylmethylamino-3-(5'-chloro-2'-toluyl-amino)-5-methoxy-tetralin and 64.5 ml (304 mM) of chloroformic acid-(−)-menthylester in toluene/2-propanol 10: 1. After stirring for 2 hours at room temperature, saturated NaCl solution is added, and the solution is extracted with ethyl acetate. The organic phases are dried over Na$_2$SO$_4$, filtered and concentrated. The resulting 180 g of raw product are chromatographed on silica gel with diethylether/hexane 3:7, whereby 119.5 g of pure diasteroisomeric mixture of formula VI are obtained.

d) A solution of 117 g (205 mM) of the diastereoisomeric ester of formula VI in ½ liter of THF is added in drops whilst cooling with ice, over the course of 30 minutes, to 15 g (689 mM) of lithium borohydride in 1 liter of THF. After stirring for 16 hours at room temperature, the preparation is cooled again to 0°, and 200 ml of ice water are slowly added. After extracting with ethyl acetate, washing with saturated NaCl solution, drying over Na$_2$SO$_4$, filtering and concentrating by evaporation, 104 g (94% of theory) of the diastereoisomeric alcohols of formula V are obtained as a yellowish foam. The raw diasteroisomeric mixture is cyclized directly.

e) (−)-[4aR,10aR]-1,2,3,4,4a,5,10,10a-octahydro-4-(4'-chloro-2'-methyl-phenyl)-1-(−)-menthyloxycarbonyl-6-methoxy-benzo[g]quinoxaline 92.5 ml of tetrabromomethane (42.5% in acetonitrile, 119.25 mM) are added in drops at 50°, over the course of 30 minutes, to a solution of 25 g (47.7 mM) of the diastereoisomeric alcohols of formula V and 31 g (119.25 mM) of triphenylphosphine in 250 ml each of toluene and acetonitrile. After stirring for 1 hour at room temperature, the solution is poured onto KHCO$_3$ solution, extracted with toluene/ethyl acetate 1:1, containing 10% isopropanol, and washed with saturated NaCl solution. The organic phases are dried over Na$_2$SO$_4$ and filtered and concentrated by evaporation. The raw product is taken up in ethyl acetate and purified preliminarily by a short column of silica gel. After chromatography on SiO$_2$ with hexane/ether 95:5, 12 g of pure title compound are obtained.

NMR (DMSO, 360 MHz) δ 0.79 (d, J=6 Hz, 3H), 0.87 (d, J=6 Hz, 3H), 0.9 (d, J=6 Hz, 3H), 1.64 (m, 2H), 1.91 (m, 3H), 2.27 (s, 3H), 2.71 (m, 1H), 2.81 (dd, J$_1$=18 Hz, J$_2$=6 Hz, 1H), 2.96 (dd, J$_2$=18 Hz, J$_2$=12 Hz, 1H), 3.20 (m, 1H), 3.65 (s, 3H), 4.57 (dd, J=12 Hz, J$_2$=5 Hz, 1H), 6.72 (d, J=8 Hz, 2H), 7.10 (t,J=9 =9 Hz, 1H), 7.26 (m, 1H), 7.33 (m, 2H).

f) (−)-[4aR,10aR]-1,2,3,4,4a,5,10,10a-octahydro-4-(4'-chloro-2'-methyl-phenyl)- 6-methoxy-1-methyl-benzo[g]quinoxaline 200 ml (200 mM) of diisobutyl aluminium hydride solution (20% in hexane) are added in drops at 0°, over the course of 15 minutes, to a solution, which is under argon, consisting of 16 g (30.5 mM) of (−)-[4aR,10aR]-1,2,3,4,4a, 5,10,10a-octa-hydro-4 -(4'-chloro- 2'-methyl-phenyl)-1-(−)-menthyloxycarbonyl-6-methoxy-benzo[g]quinoxalinin 200 ml of THF. After stirring for 2 hours at room temperature, it is cooled to 0° and slowly mixed with 75 ml of H$_2$O, then diluted with 200 ml of ethyl acetate and filtered through Hyflo. The residue of filtration is washed with toluene/ethyl acetate 1:1, containing 10% isopropanol. The flitrate is mixed with saturated NaCl solution and extracted with ethyl acetate. The combined organic phases are dried over Na$_2$SO$_4$, filtered and concentrated. The raw product is chromatographed on silica gel with ether/hexane 1:1.9.4 g of pure title compound are obtained as a white amorphous powder.

[α]$_D^{25}$=−11° (pyridine, c=0.31).

NMR (DMSO, 360 MHz) δ 1.88 (dd, J$_1$=18 Hz, J$_2$=12 Hz, 1H), 2.10 (m, 1H) 2.29 (s, 3H), 2.32 (s, 3H), 2.45 (m, 1H), 2.61 (dd, J$_1$=18 Hz, J$_2$=12 Hz, 1H), 3.12 (m, 1H), 3.20 (dd, J$_2$=18 Hz, J$_2$=5 Hz, 1H), 3.62 (s, 3,H), 6.68 (d,J=9 Hz, 1H), 6.72 (d,J=9 Hz, 1H), 7.07 (t, J=9 Hz, 1H), 7.22 (dd, J$_1$=9 Hz, J$_2$=2 Hz, 1H), 7.28 (d, J=9 Hz, 1H), 7.34 (d, J=2 Hz, 1H).

EXAMPLE 2

(−)-[4aR,10aR]-1,2,3,4,4a,5,10,10a-octahydro-4-(4'-chloro-2'-methyl-phenyl)-1-methyl-benzo[g]quinoxaline-6-ol 49.3 ml (512 mM) of BBr$_3$ are added in drops at 0°, over the course of 30 minutes, to a solution of 11.4 g (32 mM) of the compound produced in example 1 in 500 ml of CHCl$_3$. The yellowish suspension is stirred for 2 hours at room temperature. The reaction mixture is subsequently cooled to 0° again and adjusted to pH 8 with 70 ml of NH$_3$ solution (25%). Extraction with ethyl acetate, containing 10% isopropanol, drying over Na$_2$SO$_4$, filtration and concentration, yield 11.3 g of raw product. In order to produce the salt, the base is dissolved in isopropanol and methanol, mixed with 1 equivalent of 3.4N HCl in EtOH and concentrated until crystallization commences. 9.1 g of pure hydrochloride of the title compound are obtained.

M.p.: from 270° decomp.

[α]$_D^{25}$=−60° (c=0.24 in EtOH/H$_2$O 1:1)

NMR (DMSO, 360 MHz) δ 1.95 (dd, J$_1$=18 Hz, J$_2$= 11 Hz, 1H), 2.33 (s, 3H), 2.80 (dd, J$_1$=18 Hz, J$_2$=5 Hz, 1H), 2.95 (d, J=4 Hz, 3H), 6.61 (d, J=6 Hz 2H), 6.96 (t, J=9 Hz, 1H), 7.30 (s, 2H), 7.40 (s, 1H), 9.44 (s, 1H), 11.21 (b, 1H).

The following compounds wherein R$_1$ is methyl, R$_3$ is hydroxy, R$_2$ is a group of formula (a) as defined above and the configuration is (4aR, 10aR) may be produced analogously to Example 2:

| Ex. | R'$_1$ | R'$_2$ | R'$_3$ | [α]$^{20}_D$ | m.p. | salt |
| --- | --- | --- | --- | --- | --- | --- |
| 3 | H | H | H | −127° (1) | 216–218° | bis(base) tartrate |
| 4 | CH$_3$ | H | H | −73° (2) | from 280° decomp. | methanesulfate |
| 5 | CH$_3$ | CH$_3$ | H | −66° (3) | 291° decomp. | hydrochloride |
| 6 | CH$_3$ | Br | H | −44° (4) | 260° decomp. | hydrochloride |
| 7 | CH$_3$ | CH$_3$ | CH$_3$ | −58° (5) | 270° decomp. | hydrochloride |

9
-continued

| Ex. | R'$_1$ | R'$_2$ | R'$_3$ | $[\alpha]^{20}_D$ | m.p. | salt |
|---|---|---|---|---|---|---|
| 8 | CH$_3$ | F | H | −57° (6) | 250° decomp. | hydrochloride |

(1) pyridine, c = 0.15
(2) EtOH/H$_2$O 1:1, c = 0.215
(3) EtOH/H$_2$O 1:1, c = 0.325
(4) EtOH/H$_2$O 1:1, c = 0.19
(5) EtOH/H$_2$O 1:1, c = 0.275
(6) EtOH/H$_2$O 1:1, c = 0.265

EXAMPLE 9

(+)-[4aα,10aβ]-1,2,3,4,4a,5,10,10a-octahydro-6-methoxy-4-phenyl-1-n-propylbenzo-[g]quinoxaline 1 g K$_2$CO$_3$ and 360 μl (about 3.6 mM) n-propyliodide are added to 900 mg (about 3 mM) (+)-[4aα, 10aβ]- 1,2,3,4,4a, 5,10,10a-octahydro-6-methoxy-4-phenyl-benzo-[g]quinoxaline in 30 ml dimethylformamide and the reaction mixture is stirred for 42 hours at room temperature. Working up is effected by filtering through Hyflo and evaporating the tiltrate to dryness. The residue is taken up in methylenechloride containing 10% isopropanol and extracted with concentrated NaCl solution. The combined organic phases are dried over Na$_2$SO$_4$, filtered and concentrated. One obtains 1 g of the crude title compound. M.p. of the dihydrochloride: 236°–238°.

What we claim is:

1. A compound of formula I:

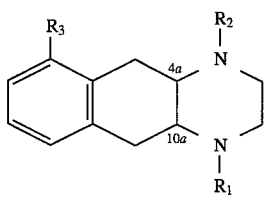

wherein R$_1$ is (C$_{1-4}$)alkyl;
R$_2$ is unsubstituted phenyl or phenyl substituted by 1 to 3 substituents selected from halogen having an atomic number of 9 to 53, (C$_{1-4}$)alkyl and (C$_{1-4}$)alkoxy; and
R$_3$ is hydroxy or (C$_{1-4}$)alkoxy,
in free base or physiologically acceptable acid addition salt form.

2. A compound of claim 1 which is (±)-[4aα,10aβ]-1,2, 3,4,4a, 5,10,10a-octahydro-6-methoxy- 4-phenyl-1-n-propylbenzo[g]quinoxaline, in free base or physiologically acceptable acid addition salt form.

3. A compound of claim 1 wherein R$_2$ is a group of formula (a)

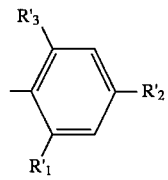

wherein

R'$_1$ is hydrogen or (C$_{1-4}$)alkyl,
R'$_2$ is hydrogen, halogen having an atomic number of 9 to 53 or (C$_{1-4}$)alkyl, and
R'$_3$ is hydrogen or (C$_{1-4}$)alkyl,
in free base or physiologically acceptable acid addition salt form.

4. A compound of claim 1 which is the (−)-[4aR,10aR]-1,2,3,4,4a,5,10,10a-octahydro-4-(4'-chloro-2'-methyl-phenyl)- 1-methyl-benzo[g]quinoxaline-6-ol, in free base or physiologically acceptable acid addition salt form.

5. A compound of claim 1 which is in cis form.

6. A compound of claim 1 which is in trans form.

7. A compound of claim 3 which is in cis form.

8. A compound of claim 3 which is in trans form.

9. A pharmaceutical composition comprising a pharmaceutically acceptable carrier or diluent and a therapeutically effective amount of a compound of claim 1, in free base or physiologically acceptable acid addition salt form.

10. A method of treating schizophrenia, which comprises administering to a subject in need of such treatment a therapeutically effective amount of a compound of claim 1, in free base or physiologically acceptable acid addition salt form.

11. A compound of claim 1 in the 4aR,10aR configuration wherein

R$_1$=CH$_3$, R$_2$=4—Cl, 2—CH$_3$-phenyl, R$_3$=OCH$_3$;
R$_1$=CH$_3$, R$_2$=phenyl, R$_3$=OH;
R$_1$=CH$_3$, R$_2$=2—CH$_3$-phenyl, R$_3$=OH;
R$_1$=CH$_3$, R$_2$=2,4-diCH$_3$-phenyl, R$_3$=OH;
R$_1$=CH$_3$, R$_2$=4-Br, 2-CH$_3$-phenyl, R$_3$=OH;
R$_1$=CH$_3$, R$_2$=2,4,6-triCH$_3$-phenyl, R$_3$=OH; or
R$_1$=CH$_3$, R$_2$=4-F, 2-CH$_3$-phenyl, R$_3$=OH;
in free base or physiologically acceptable acid addition salt form.

12. A compound of claim 1 wherein R$_1$ is methyl or ethyl; R$_2$ is unsubstituted phenyl or phenyl substituted by 1 to 3 substituents selected from chloro, bromo, fluoro, methyl, ethyl, methoxy and ethoxy; and R$_3$ is hydroxy, methoxy or ethoxy; in free base or physiologically acceptable acid addition salt form.

13. A compound of claim 3 wherein R'$_1$ is hydrogen, methyl or ethyl; R'$_2$ is hydrogen, chloro, bromo, fluoro, methyl or ethyl; and R'$_3$ is hydrogen, methyl or ethyl; in free base or physiologically acceptable acid addition salt form.

* * * * *